US 6,622,864 B1

(12) United States Patent
Debbs et al.

(10) Patent No.: US 6,622,864 B1
(45) Date of Patent: Sep. 23, 2003

(54) MOISTURE RESISTANT PACKAGE FOR STORING STERILE ITEMS

(75) Inventors: Kevin Debbs, Atlantic Highlands, NJ (US); Michael Padulsky, East Brunswick, NJ (US); Stephen N. Mercadante, South Orange, NJ (US); Donna Haag, Englishtown, NJ (US); Richard Ragula, Manalapan, NJ (US); Ronald Pilchik, Cherry Hill, NJ (US)

(73) Assignee: Osteotech, Inc., Eatontown, NJ (US)

( * ) Notice: Subject to any disclaimer, the term of this patent is extended or adjusted under 35 U.S.C. 154(b) by 0 days.

(21) Appl. No.: 09/585,121

(22) Filed: Jun. 1, 2000

(51) Int. Cl.⁷ .............................................. A61B 17/06
(52) U.S. Cl. ....................................... 206/438; 206/363
(58) Field of Search ................................ 206/363, 438, 206/439, 484, 484.1, 828; 220/367.1; 422/310; 426/124, 129, 133, 87

(56) References Cited

U.S. PATENT DOCUMENTS

| | | | |
|---|---|---|---|
| 4,280,653 A | | 7/1981 | Elias |
| 4,321,781 A | | 3/1982 | Hall |
| 4,482,053 A | * | 11/1984 | Alpern et al. ............... 206/439 |
| 4,511,035 A | * | 4/1985 | Alpern ........................ 206/363 |
| 4,533,576 A | | 8/1985 | Tanahashi et al. |
| 4,697,703 A | | 10/1987 | Will |
| 4,736,850 A | * | 4/1988 | Bowman et al. ............. 206/438 |
| 4,750,619 A | | 6/1988 | Cohen et al. |
| 5,257,692 A | | 11/1993 | Heacox |
| 5,385,229 A | | 1/1995 | Bittmann et al. |
| 5,590,778 A | * | 1/1997 | Dutchik ....................... 206/439 |
| 5,720,391 A | | 2/1998 | Dohm et al. |
| 5,772,031 A | * | 6/1998 | Landis ......................... 206/363 |
| 6,054,153 A | * | 4/2000 | Carr et al. .................... 426/124 |

OTHER PUBLICATIONS

Photographs of double blister package. The package as represented in the photographs was, upon information and belief, publicly available in or about Feb. 1999.

* cited by examiner

Primary Examiner—Luan K. Bui
(74) Attorney, Agent, or Firm—Carella, Byrne, Bain, Gilfillan, Cecchi, et al; Elliot M. Olstein; G. Glennon Troublefield

(57) ABSTRACT

A moisture resistant package for storing and transporting sterile items, such as specimens of human or animal tissue, comprises an inner tray that fits within a moisture resistant outer tray. The inner tray has a cavity for storing the specimen. The specimen is enclosed within the cavity by a non-porous inner lid that is sealed to the inner tray by an adhesive to create a moisture and microbial contaminant resistant environment that prevents moisture uptake into the specimen. The inner tray is enclosed within a complementary shaped cavity of the outer tray by an outer lid sealed to the outer tray to complete the assembly of the package. Thereafter, the package is terminally sterilized (using gas or radiation) so that the inner tray can be introduced into a sterile environment when it is removed from the outer tray. In a preferred embodiment, the inner lid includes at least one through hole to reduce the pressure differential that may occur between the outer tray cavity and the inner tray cavity, which differential may otherwise case premature lifting and separation of the inner lid from the inner tray. In addition, the outer tray and the inner tray may be formed of a sheet of transparent thermoplastic material, such as glycerol modified polyethylene terephthalate so that the specimen can be viewed without opening the package. Preferably, the sheet of material for the inner tray and the outer tray is laminated with a film of moisture barrier material and is deep drawn into a three dimensional die, while substantially maintaining the moisture barrier integrity of the trays.

49 Claims, 4 Drawing Sheets

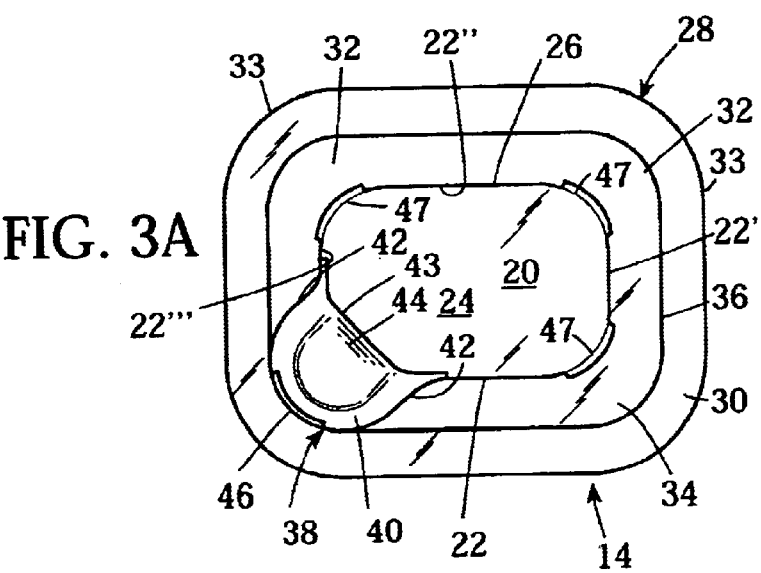
FIG. 3A
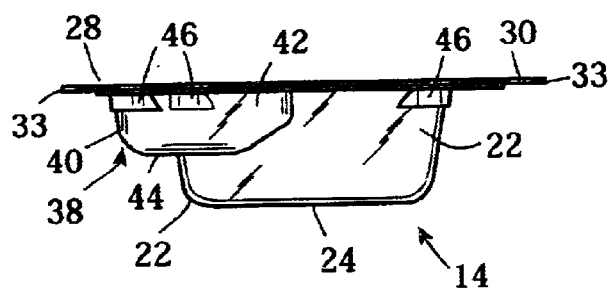
FIG. 3B
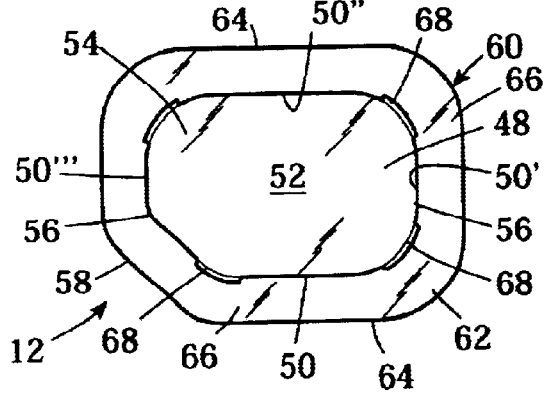
FIG. 4A
FIG. 4B

FIG. 7
FIG. 8
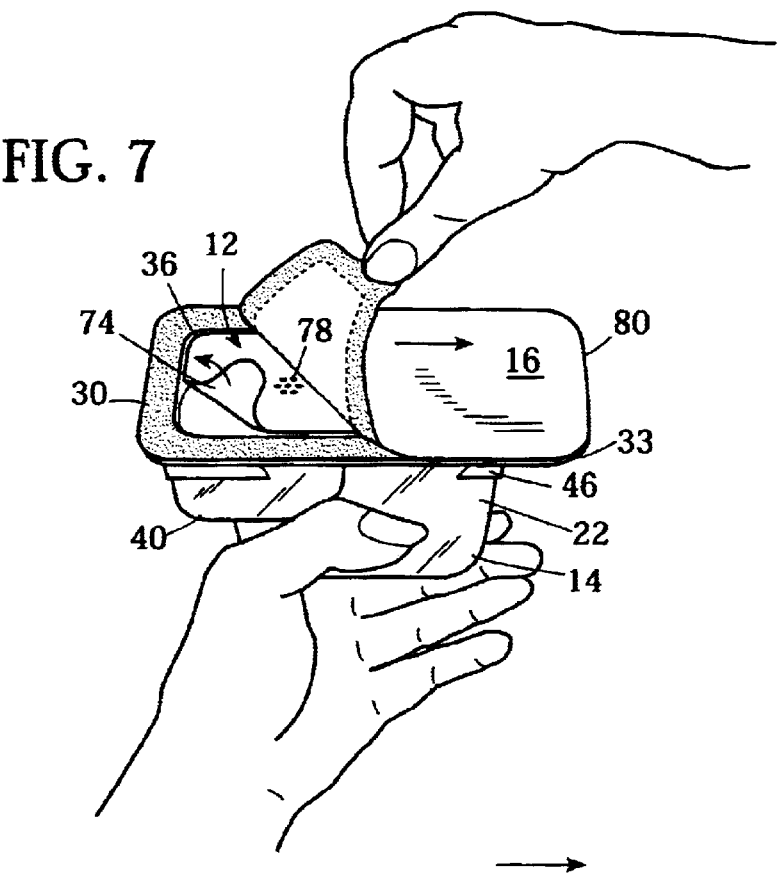
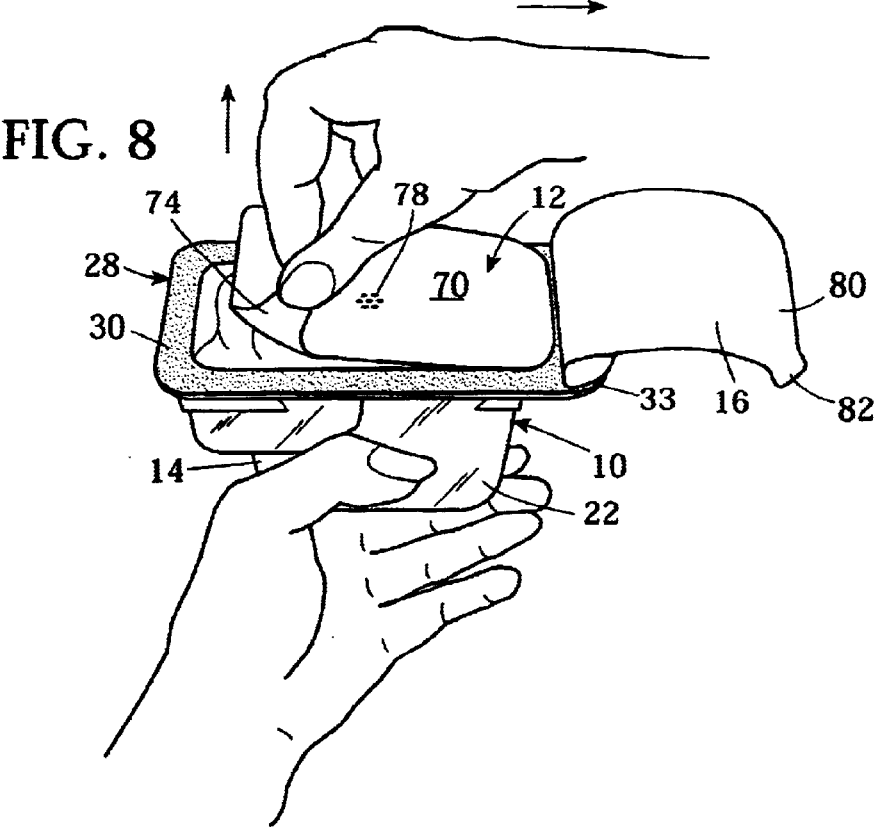

MOISTURE RESISTANT PACKAGE FOR STORING STERILE ITEMS

FIELD OF THE INVENTION

The present invention relates to packages for storing and transporting sterile items, and more particularly, relates to a nested package for storing human or animal tissue specimens or medical devices in a moisture resistant, sterile environment.

BACKGROUND OF THE INVENTION

Packages for storing items such as prosthetic medical implant devices and specimens of human or animal tissue are known in the art. Typically, prosthetic devices and human or animal tissue specimens are stored in packages until they are needed for transplant operations or for laboratory testing and analysis. Successful transplant operations or laboratory testing often turns, in part, on the sterility of the prosthetic device or tissue to be transplanted or tested. Indeed, it is well known in the art of transplant operations that the tissue to be transplanted must be kept in a sterile, bacteria free environment to avoid introducing microbial contaminants into the transplant recipient, which may lead to infections and other ailments.

Various packages for storing prosthetic implant devices, tissue specimens and other types of sterile items in a sterile environment have been proposed. For example, a typical package for a prosthetic implant device, such as a heart valve, comprises an inner package that fits into an outer package. The inner package has an open top and a recess to house the prosthetic device. To create a sterile environment, the prosthetic device is enclosed in the recess of the inner package by a cover sealed about the open top. Thereafter, the inner package is enclosed within a recess of the outer package by an outer lid sealed thereto. Variations of this type of package may include a holder retained with the inner tray to secure the prosthetic device for storage and shipment. A description of such packages can be found in greater detail in U.S. Pat. Nos. 5,720,391, 4,750,619, and 4,697,703, each of which is incorporated herein by reference.

Many packages commercially available in today's market, including those represented by the foregoing patents, are inadequate to store human or animal tissue specimens in a moisture free environment. In particular, human tissue specimens include lipids, the fatty oils, waxes, sterols, and triglycerides that are stored forms of energy in living organisms. Often, human or animal tissue is stored in a dehydrated state, with most of the moisture of the tissue removed. However, even in a dehydrated state (for example, with less than or equal to 3% moisture), residual lipids may be present in the tissue.

The presence of residual lipids in the tissue specimen threaten the integrity of the seal of the packages in which the specimen is stored. For example, many of the packages used in today's markets for storing medical devices include a container having a lid made from a porous, steam penetrable spun bonded polyolefin material, such as Tyvek available from Dupont DeNemours, having an adhesive coating. The porous material allows the package, together with the medical device enclosed therein, to be sterilized while in an assembled condition by forcing steam through the lids. However, when packages with lids made of porous material are used to store specimens of human or animal tissue, problems arise. In particular, the porous material acts as a sponge and actually begins to draw out and absorb the residual lipids that are present in the tissue being stored. Over time, the fatty oils associated with residual lipids that are absorbed by the porous material begins to dissolves the bond between the adhesive coating of the lid and the container of the package. As a result, the lid will begin to separate from the container, thereby exposing the dehydrated tissue specimen to moisture and microbial contaminants. The moisture is then absorbed by the tissue specimen which, over time, reduces the shelf-life or duration over which the tissue may be stored. Accordingly, packages having lids made of porous material suffer from an inability to prevent moisture uptake into the tissue specimen.

Various envelope packages have been proposed as a solution to the problem of storing human tissue specimens. A typical package for storing human tissue specimens is made of a double envelope comprising a sealed inner envelope for the specimen that is ultimately deposited and sealed in an outer envelope. Similarly, triple envelope packages have been also proposed. Triple packages include three sterilized envelopes, that is, an innermost envelope, an outermost envelope, and an intermediate envelope. The innermost envelope is made of plastic and stores the specimen. The innermost envelope is then stored in the intermediate envelope, also made of plastic material, and both envelopes are stored in the outermost envelope to complete the package. An example of a three-envelope package is described in greater detail in U.S. Pat. No. 5,257,692, which is incorporated herein by reference.

However, both the double and triple envelope packages described above are inadequate to store human tissue. Indeed, the envelope package shown in the '692 patent is used to cryopreserve tissue specimens in a coolant medium, such as liquid nitrogen. As such, the structure and attributes of the package must be able to withstand extremely low temperature conditions and resist liquid nitrogen seepage, in order to accomplish the storage of human tissue specimens. Moreover most of the double or triple envelope packages commercially available are not concerned with preventing moisture uptake into the tissue. If the amount of moisture absorbed by the tissue specimen exceed acceptable regulatory standards for moisture, the shelf-life of the specimen would be violated.

Although human or animal tissue specimens may be packaged, stored and transported in glass bottles, packages of this sort suffer from several limitations. For instance, the specimens are typically vacuumed packed in an airtight glass containers. The glass containers are susceptible to becoming damaged during shipping and handling, which can lead to a loss of pressure or vacuum. As a result of a loss of pressure, the specimen may become exposed to moisture or microbial contaminants. As another limitation, the outer surface of the glass containers are often non-sterile. As such, the glass containers cannot be introduced into a sterile field, such as an operating room area. Moreover, the non-sterile outer surface of the glass containers creates a risk of contaminating the specimen when the package is opened and the specimen is removed. Furthermore, as an practical matter, the lids used to seal the glass packages are extremely difficult to remove because they must be secured to the bottle tightly to prevent microbial contaminants from attacking the specimen. The tightness of the lids becomes an inconvenience, particularly during a transplant operation, when quick access to the specimen to be transplanted is critical.

Accordingly, it is desired to provide a package for storing and transporting sterile items, particularly human or animal tissue specimens or medical devices, in a moisture resistant, sterile environment. It is also desired to provide a package that can store and transport human or animal tissue specimens under normal ambient temperatures or conditions. It is also desired to provide a package made of material that can be terminally sterilized (using gas,, radiation or other techniques) so that the package and its contents can be introduced into a sterile field. It is also desired to provide a package that is light-weight and easy to use.

SUMMARY OF THE INVENTION

The present invention relates to a moisture resistant package for storing and transporting sterile items, such as specimens of human or animal tissue or medical devices. The package comprises an inner tray that fits within a moisture and microbial contaminate resistant outer tray. The inner tray has a cavity for storing the specimen. The specimen is enclosed within the cavity by an inner lid made of nonporous material that is sealed to the inner tray by an adhesive. The nonporous material helps to prevent moisture uptake into the specimen. The inner tray is enclosed within a complementary shaped cavity of the outer tray by an outer lid sealed to the outer tray, thereby creating a moisture resistant, sterile environment.

In a preferred embodiment, both the inner tray and the outer tray are transparent so that the specimen can be viewed prior to opening the package. In addition, the inner lid may include at least one hole. The hole is provided to reduce the pressure differential that may occur between the ambient pressure of the cavity of the outer tray and the pressure within the cavity of the inner tray, which may otherwise cause premature lifting and separation of the inner lid from the inner tray.

In an alternative embodiment, the inner lid includes a tab that is folded over to overlie the inner lid when the package is closed. The tab automatically unfolds and springs away from the inner lid when the package is opened for easy grasping and removal of the inner tray from the outer tray.

BRIEF DESCRIPTION OF THE DRAWINGS

For the purpose of illustrating the invention, there is shown in the drawings an embodiment of the invention which is presently preferred; it being understood, however, that this invention is not limited to the precise arrangements and instrumentalities shown.

FIG. 3A is a top plan view and FIG. 3B is a side elevation view of the outer tray of the package shown in FIGS. 1 and 2.

FIG. 4A is a top plan view and FIG. 4B is a side elevational view of the inner tray of the package shown in FIGS. 1 and 2.

FIGS. 6 through 8 illustrate the stages for opening the package shown in FIG. 1.

DETAILED DESCRIPTION OF THE INVENTION

Figure 1:
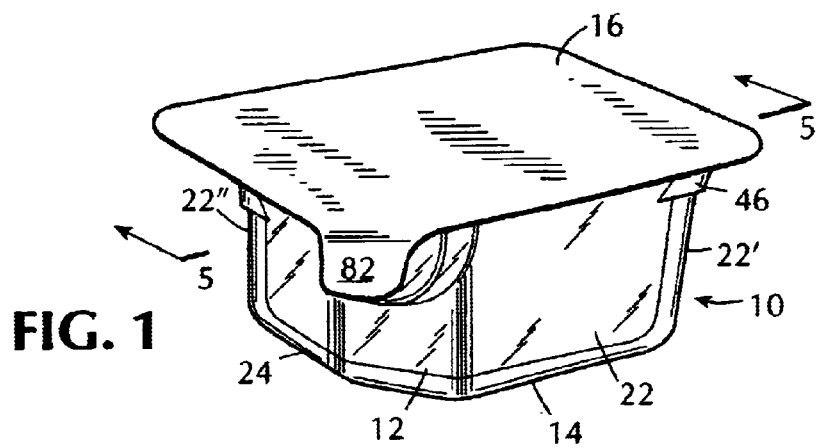
FIG. 1 is an isometric view of a moisture resistant package in accordance with the present invention.

While the invention will be described in connection with a preferred embodiment as shown in the drawings, it should be understood that the invention is not limited to the specific embodiment shown. On the contrary, the invention is intended to cover all alternatives, modifications and equivalents as may be included within the spirit and scope of the invention, as defined by the appended claims.

Referring now to the drawings, where like elements are identified by like numerals, there is shown in FIG. 1 an exemplary embodiment of a moisture resistant package 10 of the present invention. The package 10 is provided to store, preserve, and maintain in a sterile, moisture resistant, and microbial resistant environment sterile items (not shown), such as human, animal, biological, marine or agricultural specimens, which may be in the form of organs, tissues, allografts and the like. In particular, the package 10 is provided for storing and transporting human or animal tissue specimens in a moisture resistant environment, so that the specimen may be stored under normal ambient temperatures or conditions without cryopreservation or the use of similar cooling mediums or techniques.

As detailed below, the package 10 advantageously prevents moisture uptake into the tissue specimen, which helps preserve the viability and prolong the period of time over which the tissue specimen may be stored. The package 10 of the present invention may be used with a specimen that is aseptically sterilized using pre-sterilized components known in the art so that specimen is sterile when placed in the package 10. In the alternative, the package 10 of the present invention may also be terminally sterilized with the specimen of human or animal tissue stored therein after the package 10 has been assembled. As used herein, the term "terminal sterilization" is meant to include the procedure of sterilizing the package 10, its components and the specimen or sterile item at the end of the assembly process using gas, radiation (preferably gamma), gas plasma or other techniques known in the art. Although the package 10 is described herein with respect to storing a human or animal tissue specimen, it should be understood, of course, that the package 10 may be used to store other sterile items, such as prosthetic medical implant devices.

Figure 2:
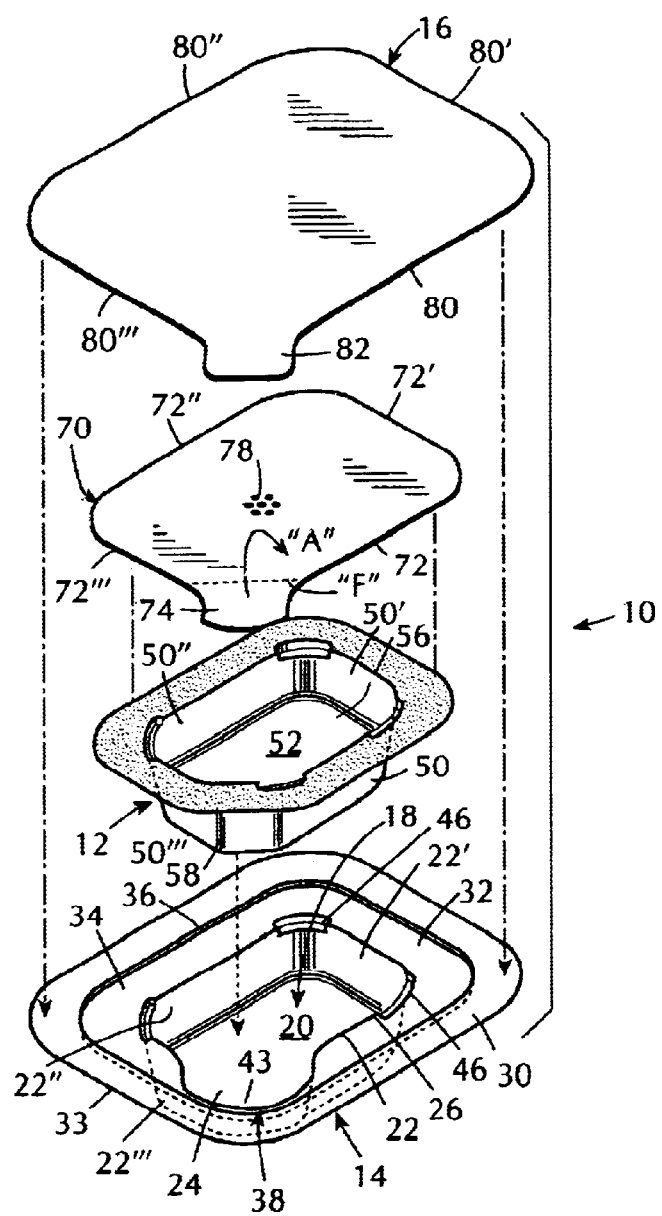
FIG. 2 is an exploded isometric view of the package shown in FIG. 1.

As shown in FIGS. 1 and 2, the package 10 comprises a moisture resistant, blister-type package, namely an inner tray 12 that fits and is removably disposed within a moisture resistant outer tray 14. The outer tray 14 is a unitary, one piece integrally formed open-top thermoplastic container that is enclosed by a lid 16. The outer tray 14 includes a recess or cavity 20 (FIG. 2) that forms a first cavity of the package 10 exhibiting a first pressure. The cavity 20 is formed by a first plurality of upstanding side walls 22, 22', 22", and 22'" of the package 10 joined to a closed bottom wall 24. Wals 22, 22', 22", 22'" and 24 form the blister portion of the outer tray 14. Wals 22, 22', 22", and 22'" are joined at the corners and further define opening 18 for access to cavity 20 and a peripheral edge 26.

As best seen in FIGS. 2 and 3A, the outer tray 14 is associated with a sealing element 28 that forms the first sealing element of the package 10. The sealing element 28 is used to enclose the contents of cavity 20 in a moisture resistant, sterile environment. Sealing element 28 comprises an outer planar support flange 30 and an inner planar support flange 32. Flange 30 has a peripheral edge 33 and is joined to support flange 32. Flange 32 is supported by and projects outwardly from and normal to walls 22, 22', 22", and 22'". Flange 32 extends generally around the periphery of edge 26, disposed in a plane slightly below shoulder flange 30 to form a recessed seat 34. Seat 34 terminates at an annular ridge 36 that is disposed intermediate support flange 32 and shoulder flange 30. Ridge 36 and seat 34 form a recess to help keep the inner tray 12 nested within the outer tray 14.

The spacing intermediate ridge 36 and edge 33 of the shoulder flange 30 forms an adhesive receiving sealing area for receiving adhesives or other sealing material or means to attach lid 16 to the outer tray 14.

Preferably, the outer tray 14 includes a recessed thumb or finger receiving portion 38 that is partially formed within seat 34. Portion 38 facilitates the removal of the inner tray 12 from within the outer tray 14. As depicted in FIGS. 2, 3A, and 3B, portion 38 has a bulbous portion 40 that projects diagonally outwardly from two adjacent walls 22 and 22'''. The shape of portion 40 is formed by opposed side wails 42 that are joined to a bottom wall 44 located below flange 30, about half-way down walls 22 and 22'''. Portion 40 includes side wall 43 that is joined on opposite sides to walls 22 and 22'''. Wall 43 is disposed at an angle relative to walls 22 and 22''', preferably about 45°. The interior of portion 40 provides a recess that communicates with and provides finger access to the recess 20 of the outer tray 14 so that the inner tray 12 can be easily manually removed.

The outer tray 14 is made from a preferably transparent sheet or film of semi-rigid, but flexible thermoformable plastic resin having moisture barrier properties. The resin forming the outer tray should be capable of being sterilized using techniques known in the art, including gas, radiation, gas plasma or the like. The resin forming the outer tray 14 should also be able to withstand the rigors of shipping and handling of the package 10.

Preferably, the outer tray 14 is made of a glycerol modified polyethylene terephthalate (PETG) that is laminated with a moisture barrier film. PETG is a substantially transparent amorphous polymer, in which a second glycol cyclohexanedimenthanol is added during the polymerization stages to make the modification. The second glycol is added in the appropriate portion to produce an amorphous polymer. PETG will not crystallize and thus offers wider processing latitude than conventional crystallizable polyesters. As such, plasticizers or stabilizers are not required for PETG, which offers an excellent combination of clarity, toughness and melt strength which makes it very useful for the end user. The sheet of PETG material should have a thickness that ranges from about 7 mils to about 50 mils (i.e., from about 178 microns to about 1270 microns). PETG is commercially available in the market from several manufactures, such as Kodar PETG copolyester 6763 available from Eastman Kodak. Although PETG is preferably used for the outer tray 14, other plastics may also be used, such as polyvinyl chloride (PVC), as one alternative example.

The PETG is coated with a layer of film material having moisture barrier properties. Preferably, the film of moisture barrier material is preferably laminated to the PETG (on either the inner or the outer side of the material) using adhesives or other techniques known in the art. The moisture barrier film is provided to prevent moisture uptake or water from being absorbed or transferred to the package 10 or its contents. Preferably, the moisture barrier material applied to the PETG is a 2.00 mil thick sheet of a thermoplastic resin having high performance barrier film properties, such as polyethylene, PVC, and similar types of homopolymers that are typically used in the pharmaceutical and medical markets. For example, set forth below in Table 1 is an example of the properties of the type of homopolymer that may be laminated with the PETG, it being understood that the present invention is not limited to the specific values set froth in the table:

TABLE 1

Structure Of The Resin:
About 2.0 mils (51 μ) film at about 73° F. - 50% RH

| Properties | English | Metric |
| --- | --- | --- |
| Specific Gravity | about 2.11 | |
| Yield | about 6,570 in²/lb | about 9.33 m²/kg |
| Haze | about <1% | |
| Crystalline Melting Point | about 412° F. | about 211° C. |
| Dimensional Stability (@ 10 mins.) | at about 300° F.: +5 to +10% | at about 149° C.: −5 to −10% |
| Tensile Strength | MD: about 6,000 to about 9,000 psi | about 41 to about 62 MPa |
| | TD: about 4,500 to about 7,500 psi | about 31 to about 52 MPa |
| Elongation | MD: about 150% to about 250% | |
| | TD: about 200% to about 300% | |
| Modulus, Secant | MD: about 150,000 to about 190,000 psi | MD: about 103 to about 131 MPa |
| | TD: about 150,000 to about 190,000 psi. | TD: about 103 to about 131 MPa |
| | about 4,500 to about 7,500 psi | about 31 to about 52 MPa |
| Tear Strength (Graves) | MD: about 325 to about 375 gms/mil | |
| | TD: about 275 to about 325 gms/mil | |
| Water Vapor Transmission Rate @ about 100° F. (37.8° C.)/100% RH | about 0.008 grms/100 in²/day | about 0.12 grms/m²/day |

The exemplary moisture barrier film having the properties set forth in Table 1 is commercially available from several manufactures, such as ACLAR available from Honeywell.

After the moisture resistant film is added to the PETG, the laminated sheet of material is then manufactured into a three dimensional product to form the outer tray 14 using a deep drawing processing technique. Prior to the present invention, its has been difficult, if not impossible to deep draw plastic material coated with a film of moisture barrier material to produce a three dimensional object, such as a blister package, in which the integrity of the moisture barrier properties of the package are substantially maintained. Often, when the prior art coated plastic material is drawn into a deep drawing female die cavity by a complementary shaped male punch, the film of moisture barrier material would bulge, crack or begin to separate from the underlying PETG material. The cracks in the film of moisture barrier material expand after processing, thereby creating openings that allow moisture to be absorbed by the product or otherwise increase the moisture or water vapor transmission rate.

However, surprisingly, according to a method of manufacturing the package 10 of the present invention, the problems associated with deep drawing the coated PETG into a three dimensional product while substantially maintaining the moisture barrier integrity of the film is substantially alleviated. In particular, by selecting the thickness of the film of moisture barrier material as well as the thermoforming range of the coated PETG lamination, cracks and other imperfections that otherwise jeopardize the moisture barrier properties of the PETG lamination are substantially precluded. In addition, the moisture vapor transmission rate can be advantageously controlled by the selection of the properties of the PETG lamination for a given implementation.

One of ordinary skill in the art can select the particular parameters for a given implementation. For example, set forth below in Tables 2 and 3 are two examples of the physical properties the PETG lamination, having a layer of moisture barrier film material. As used in Tables 2 and 3 below, the word "FILM" is a short reference to the layer of moisture barrier film material that was discussed above, in which an exemplary type of material is set forth in Table 1. It should be understood, of course, that the present invention is not limited to the specific values set forth in each of the following tables:

TABLE 2

| Lamination | About 835 PVC/ About 50 FILM | about 25.0 mil PETG/ about 2.0 mil FILM |
| --- | --- | --- |
| General | | |
| Color | Clear Tint | Clear Tint |
| Haze | about 2% | about 2% |
| Specific Gravity | about 1.36 g/cm$^3$ | about 1.36 g/cm$^3$ |
| Total Thickness | about 686 | about 0.0270 |
| Thickness Tolerance | about ±10% | about ±10% |
| Maximum Roll Width | about 1.1 m | about 42" |
| Roll Width Tolerance | about ±1.5 mm | about ±1/18" |
| Nominal Yield | about 1,074 m$^2$/kg | about 755 in$^2$/lb |
| Thermal | | |
| Dimensional Stability | about ±4% (30 minutes @ 140° C.) | about ±4% (30 minutes @ 284° F.) |
| Thermoforming Range | about 100–160° C. | about 212–320° F. |
| Barrier | | |
| Moisture Vapor Transmission Rates (38° C., 90% RH) | about 0.11 g/m$^2$/24 hrs | about 0.007 g/100 in$^2$/24 hrs |

TABLE 3

| Lamination | About 762 PVC/ About 50 FILM | about 30.0 mil PETG/ about 2.0 mil FILM |
| --- | --- | --- |
| General | | |
| Color | Clear Tint | Clear Tint |
| Haze | about 2% | about 2% |
| Specific Gravity | about 1.35 g/cm$^3$ | about 1.35 g/cm$^3$ |
| Total Thickness | about 813 | about 0.0320 |
| Thickness Tolerance | about ±10% | about ±10% |
| Maximum Roll Width | about 1.1 m | about 42" |
| Roll Width Tolerance | about ±1.5 mm | about ±1/18" |
| Nominal Yield | about 0.913 m$^2$/kg | about 642 in$^2$/lb |
| Thermal | | |
| Dimensional Stability | about ±4% (30 minutes @ 140° C.) | about ±4% (30 minutes @ 284° F.) |
| Thermoforming Range | about 100°–160° C. | about 212°–320° F. |
| Barrier | | |
| Moisture Vapor Transmission Rates (38° C., 90% RH) | about 0.11 g/m$^2$/24 hrs | about 0.007 g/100 in$^2$/24 hrs |

Returning to FIGS. 3A and 3B, the outer tray 14 preferably includes a plurality of lugs 46 that project outwardly from the corner of adjacent walls 22, 22', 22", 22'" and the bulbous portion 40, just below the shoulder flange 32. The lugs 46 facilitate placement of the inner tray 12 into the outer tray 14 and are designed for material handling stacking of individual inner trays 12 and individual outer trays 14 with each other. Each lug 46 includes a complementary shaped recess (not shown) to receive complementary shaped lugs associated with of the inner tray 12 so that the inner tray 12 is attached and will remain as stable as possible once nested within the cavity 20 of the outer tray 14. The lugs 46 may also be useful in stacking the outer tray 14 one on top of each other for storage.

Turning now to FIGS. 4A and 4B, the inner tray 12 is shown. The inner tray 12 is constructed similar to the outer tray 14, preferably being a unitary, one piece integrally formed thermoplastic container having an open top. The inner tray 12 has a recess or cavity 48 that forms a second cavity of the package 10 exhibiting a second pressure. The cavity 48 is provided to releasably retain the specimen (not shown) stored within the inner tray 12. Cavity 48 is formed by a plurality of second upstanding side walls 50, 50', 50", 50'" joined to a bottom wall 52, which form the blister portion of the inner tray 12. Walls 50, 50', 50", 50'" are joined at the corners to form an opening 54 for access to cavity 48, defined by edge 56 of the inner tray 12 formed by the upper portion of walls 50. The inner tray 12 also includes a truncated portion 58 that is disposed at an angle relative to walls 50 and 50'", preferably at about 45°. The truncated portion 58 is shaped complementary to side wall 43 of the bulbous portion 40 of the outer tray 14 so that the inner tray can be closely nested within the outer tray 12.

The inner tray 12 includes a sealing element 60 supported by walls 50, 50', 50", and 50'". The sealing element 60 comprises a shoulder flange 62 that projects outwardly from and normal to walls 50, 50', 50", and 50'" terminating in at a peripheral edge 64 positioned outwardly from edge 56 of the cavity 48. The flange 62 is shaped complementary to seat 34 of the outer tray 14, such that edge 64 will be positioned inwardly or abut ridge 36, which facilitates the nesting relationship of the inner tray 12 and outer tray 14 when the package 10 is assembled. Flange 62 includes a sealing surface area 66 that receives an adhesive or other sealing material.

Preferably, the inner tray 12 includes a plurality of lugs 68 that are formed at the corners of walls 50. The lugs 68 are shaped complementary to mate with the recess of the lugs 46 of the outer tray 12 to facilitate the nesting engagement of the inner tray 12 within the outer tray 14 when the package 10 is assembled and closed. In that way, the lugs 68 help to keep the inner tray 12 as firmly and as stable as possible in the outer tray 14.

The inner tray 12 is made from a sheet or film of preferably transparent relatively stiff, semi-rigid, but flexible thermoformable plastic resin, such as the transparent glycerol modified polyethylene terephthalate (PETG) used to make the outer tray 14. The plastic resin material should be capable of being sterilized using techniques known in the art, including gas, radiation, gas plasma, and the like. The resin forming the inner tray 12 should also be flexible enough to absorb the impact or the rigors of shipping and handling. The PETG may include a film of moisture barrier material laminated thereon, similar to the ACLAR laminated to the PETG used to make the outer tray 14 moisture resistant. Other suitable resins, such as PVC, may also be used.

The specimen to be stored within the cavity 48 is enclosed by a lid 70 secured to the inner tray 12. As shown in FIG. 2, the lid 70 is a one-piece, substantially flat cover made from a sheet of nonporous lidding material, that is able to withstand sterilization, using gas, radiation (gamma), gas plasma, and the like. The lid 70 has side edges 72, 72', 27", and 72'" that are shaped complementary to shoulder flange 62 of the inner tray 12, such that edges 72, 72', 27", and 72'" will coincide with edges 64 of the flange 62 when the lid 70 is sealed to the inner tray 12. The lid 70 may be releasably sealed or secured to shoulder flange 62 using adhesives, discussed below.

Preferably, a tab 74 is associated with the lid 70. The tab 74 is an integrally formed flap or short strip to facilitate peeling off the lid 70 from the inner tray. The tab 74 projects outwardly from the lid 70 at the corner of adjacent sides 72' and 72'". When the package 10 is closed, the tab 74 is folded over about a pre-scored, lightly perforated fold line "F" (in a accordance with arrow "A") until it overlies the lid 70 in a closed, storage position, best seen in FIG. 5. Folding the tab 74 will create a simulated, truncated portion 76 (not shown in FIG. 2) that corresponds to the truncated portion 58 of the inner tray 12 so that there will be little, if any overhang by the tab 74. When the package 10 is opened, the tab 74 unfolds automatically, springing away from lid 70 as it moves from the closed position toward an upright position (See FIG. 7). As the tab 70 approaches or even exceeds the upright position, it can be easily grasped by the user to remove the inner tray 12 from within the cavity 20 of the outer tray (See FIG. 8). The tab 74 is also useful to facilitate peeling off the lid 74 from the shoulder flange 62 to expose and provide access to the contents of the cavity 48, namely the specimen.

As shown in FIG. 2, the lid 70 preferably includes at least one or a plurality of through or breather holes 78 (six shown) formed therein. Holes 78 help to equalize the first pressure of the cavity 20 of the outer tray 14 relative to the second pressure of the cavity 48 of the inner tray 12. Equalizing the pressure will help to prevent the lid 70 from separating prematurely from the inner tray 12 due to pressure differentials that may build up during transportation or storage of the package 10. Premature lifting of the lid 70 inside the package 10 may cause the contents of the cavity 48 (namely the specimen) to become exposed to a non-sterile environment if, for example, the outer tray 14 is mistakenly opened in a non-sterile environment.

Holes 78 may be formed using lasers or other techniques or mechanical devices known in the art for making a hole in a sheet of material, such as a pneumatically driven needle. The holes 78 have a preferable diameter of anywhere in the range of about 15 microns to about 20 microns. The size of the holes 78 is calculated based on the volume of the cavity 48 and expected pressure differential magnitudes. Although six holes 78 are shown in FIG. 2, only one is needed. Because the holes 78 only communicate the air in the cavity 20 (which is sterile) with the air in the cavity 48, the holes 78 will not jeopardize the sterility of the specimen stored in the cavity 48 of the inner tray provided that cavity 20 remains sterile.

Preferably, the lid 70 is made from medical packing grade lidding material, such as non-porous high density polyethylene (HDPE). The HDPE used for the lid 70 should be of medium molecular weight, having maximum stiffness, good heat resistance, and low machine direction tear. A typical sheet of HDPE that may be used to make the lid 70 may include optical properties such as about 12% gloss at 45° and about 68.5% haze. As to the physical properties, the HDPE material may have a tensile strength of about 22,872 pounds per square inch, an ultimate elongation of about 432%, and a coefficient of friction (slip) in the range between about 0.25 to about 0.45.

The lid 70 is sealed to the inner tray 12 by a non-toxic hot melt heat sealable adhesive coating having high tack. Preferably, the adhesive is a 100% solids, EVA based hot melt adhesive modified with resins and waxes. The adhesive is applied to the unexposed surface of the lid 70 or to the shoulder flange 62. The adhesive coating is preferably applied in a uniform dot pattern to provide high tack and peelable seal quality. Typically, the adhesive has a coat weight of about 12 pounds per ream (about 22.4 grams per meter squared), and a peal strength of about 180° peel at about 10.14 pounds per inch width (about 1812 grams per centimeter width). The adhesive has a blue tint that is activated during the heat sealing process which can be interpreted as indicating the seal integrity of the inner tray 12. The adhesive helps to maintain the contents of the cavity 48, such as the specimen, in a moisture resistant and microbial contaminant resistant, sterile environment.

There are a number of suitable adhesives that can be used with the package 10 of the present invention. Adhesives known in the art for securing and sealing a nonporous peelable lid to a substrate, such as a container, are commercially available from a number of manufactures. The particular type of adhesive that may be used to secure the lid 70 to the inner tray 12 may be determined empirically by one of ordinary skill in the art for a given implementation, by the selection of the coat weight, peel strength, bonding strength, and other properties of the adhesive that is desired.

Other suitable adhesives for attaching and sealing the inner lid 70 to the inner tray 12, to help maintain the moisture resistant and microbial resistant environment of the cavity 48, may also be used. For example, in an alternative embodiment, it is contemplated that adhesives or other sealing material or means that resist breakdown when exposed to human or animal tissue or lipids may be used in keeping with the scope of the present invention. Such lipid resistant adhesive material can be applied or coated to the inner lid 70. It is contemplated that the bonding strength of the lipid resistant adhesive will not significantly degrade when exposed to residual lipids such as to permit the inner lid 70 to separate from the inner tray 12 and expose the specimen to moisture or microbial contaminants. The adhesive will contribute to the ability of the package 10, particularly the inner tray 12, to maintain the specimen in a moisture resistant environment. Adhesives of this sort may be determined empirically by one of ordinary skill in the art for a given implementation, by the selection of the coat weight, the peel strength, the bonding strength, and other properties of the adhesive, in view of the type of tissue specimen to be stored in the inner tray 12.

After the lid 70 is sealed to the inner tray 12, the inner tray 12 is enclosed within the cavity 20 of the outer tray 14 by an outer lid 16 (See FIG. 1). Outer lid 16 is a one-piece, substantially flat cover made from a sheet of lidding material. The lid 16 has side edges 80, 80', 80", 80''' and is shaped complementary to shoulder flange 30 of the outer tray 14. The lid 16 preferably includes a tab 82. Tab 82 is a flap or short strip of material that is attached to and projects outwardly from the corner of adjacent sides 80 and 80''' to facilitate peeling back the lid 16 to exposed the inner tray 12 nested within the cavity 20.

The lid 16 is made of a non-porous high moisture barrier, puncture resistant flexible lamination. The material used for the lid 16 should be able to withstand sterilization, using gas, radiation (gamma), gas plasma, and the like. The material used for the lid 1 should also have sufficient puncture resistance qualities and be preferably opaque for light barrier. The following physical data set forth in Table 4 is typical of the type of lamination that may be used for the lid 16; it being understood that the scope of the invention is not limited to the precise data set forth therein:

TABLE 4

Lamination

| Structure | Caliper | Weight (lbs./3MF$^2$) | (gm/M$^2$) |
|---|---|---|---|
| Polyester | about .048 mils | 12.0 $\mu$ | about 10.4 lbs | 17.0 gms |
| LDPe | about 0.70 mils | 17.6 $\mu$ | about 10.0 lbs | 16.3 gms |
| Foil | about 1.00 mils | 25.0 $\mu$ | about 42.1 lbs | 68.6 gms |
| EAA | about 0.50 mils | 12.5 $\mu$ | about 7.5 lbs | 12.2 gms |
| LLPe | about 2.00 mils | 50.0 $\mu$ | about 28.8 lbs | 47.0 gms |
| Heat Seal | about 0.35 mils | 8.8 $\mu$ | about 4.0 lbs | 6.5 gms |
| TOTAL | about 5.03 mils | 125.9 $\mu$ | about 102.8 lbs | 167.6 gms/M$^2$ |

The exemplary lamination set forth in Table 4 has a yield strength of about 4,202 square inches per pound or about 5.96 M$^2$/Kg. The seal strength will depend upon the sealing conditions, but the seal range will be anywhere from about 220° F. to about 400° F. for about 0.5 seconds to about 3.0 seconds at about 20 pounds per square inch to about 80 pounds per square inch. (This translates in metric units to about 107° C. to about 204° C. for the same time period at about 2.1 kilograms per centimeter squared.) Under these conditions, the puncture resistance will be about 12.2 pounds.

The foil that is used as part of the lamination, the third ingredient set forth in Table 4, is generally impermeable and should about 0.001 inches thick or thicker. The 0.001 inch thick foil laminate provides an impermeable barrier to gas and moisture. Foil about 0.00035 inches thick has a water vapor transmission rate of about 0.002 grams or less per 1000 square inches at about 24 hours at 100° F. However, the vapor transmission rate drops to about zero when a foil about 0.00035 inches thick is laminated to an appropriate moisture barrier film. Foil is preferred because its natural oxide coating reduces corrosion, is generally non-soluble in water, and will not absorb water or other liquids. The foil can be sterilized when heat treated in production. Furthermore, the smooth metallic surface of the foil will resist permeability of most contaminants and moisture, which is critical to maintaining sterility.

The lid 16 is releasably sealed or secured to the shoulder flange 30 of the outer tray 14 by adhesives using techniques generally known in the art. Preferably, the adhesive provides a moisture barrier that avoids any creep when it is used to attach the lid 16 to the flange 30 of the outer tray 12. A typical adhesive should weigh about 12 lbs per ream or about 19.2 grams per meter squared. The peel strength of the adhesive should be about 3.69 pounds per inch width or about 660 grams per centimeter. The adhesive is applied to the sealing area 35 of the shoulder flange 30. The adhesive will help maintain the contents of the cavity 20 in a moisture resistant and microbial resistant, sterile environment.

There are a number of suitable adhesives that can be used to secure the lid 16 to the outer tray 14. Adhesives known in the art for securing and sealing a peelable lid to a substrate, such as a container, are commercially available from a number of manufactures. The particular type of adhesive that may be used to secure the lid 16 to the outer tray 14 may be determined empirically by one of ordinary skill in the art for a given implementation, by the selection of the coat weight, the peel strength, the bonding strength, and other properties of the adhesive that is desired.

In a typical commercial application, the package 10 of the present invention is assembled using the following steps. For example, the specimen to be stored in the package 10, such as human tissue or organs, is selected. The specimen may be sterilized aseptically through a series of antibiotic soaks and washes before the specimen is place into the inner tray 12. Once the specimen is sterilized, it then placed into the cavity 48 of the inner tray 12 and is enclosed by lid 70. Preferably, adhesive material that resists break-down when exposed to lipids is applied to the sealing area 66 of the shoulder flange 62 of the inner tray 12. After the adhesive is applied, the lid 70 is heat sealed to the shoulder flange 62 to enclose the specimen mi a moisture resistant, sterile environment within the inner tray 12. The heat sealing of the adhesive will create a blue tint, indicating the seal integrity of the lid 70 to the inner tray 12. Once sealed, the lid 70 will prevent the specimen from being exposed to moisture or other microbial contaminants during storage and transportation of the package 10.

Figure 5:
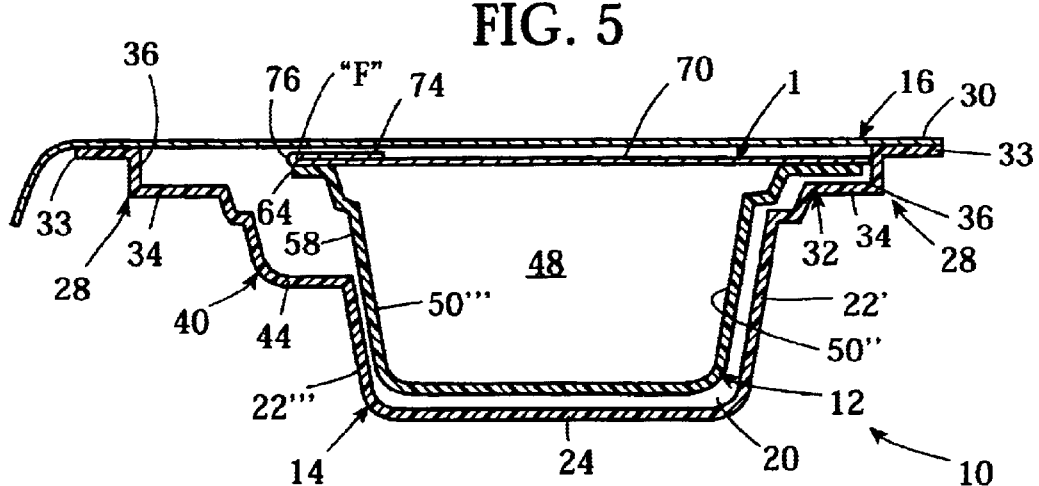
FIG. 5 is a side elevation-section view of the package shown in FIG. 1, taken along lines 5—5.

Next, the inner tray 12 is placed into the outer tray 14. The blister portion of the inner tray 12 defined by walls 50, 50', 50", 50''' should fit within the cavity 20 of the outer tray 14 in a pre-selected alignment. The inner tray 12 should be moved relative to the cavity 20 of the outer tray 12, until the truncated cut-away portion 58 of the inner tray 12, is aligned relative to the side wall 43 of the outer tray 14. Once the inner tray 12 is in the pre-selected alignment, the inner tray 12 is moved toward the outer tray 14 until the blister portion of the inner tray 12 is nested within the cavity 20 of the outer tray 14. The inner tray 12 should be pushed into the outer tray 14 far enough until the shoulder flange 62 of the sealing element 60 of the inner tray 12 is nested within the seat 34 of the outer tray (See FIG. 5). As shown in FIG. 5, the edge 64 of shoulder flange 62 will be positioned inwardly of the ridge 36 of the sealing element 28 of the outer tray 14.

Next, the tab 74 should be folded inwardly about fold line "F" in a direction according to arrow "A" until it overlies the inner lid 70, as best seen in FIG. 5. After the tab 74 is in position, the outer lid 16 is secured to the sealing area of the outer tray 14 using an adhesive to enclosed the inner tray 12 in the cavity of the outer tray 14. Securing the lid 16 to the outer tray 14 will then enclose the inner tray 12 in a moister resistant, microbial barrier to prevent the specimen from being exposed to moisture or microbial contaminants during storage and transportation of the package 10.

Thereafter, the package 10 is boxed into a container and the box, with the package 10, is then stored until needed. The box, including the inner tray 12, outer tray 12, and specimen may then be terminally sterilized using gas, gas plasma, radiation (gamma) or other techniques known in the art. Terminal sterilization will sterilize the package 10, its components, and the specimen so that at least the inner tray 12 of the package 10 can be introduce into a sterile field, such as an operating room or surgery area without further sterilization. It is contemplated, of course, that the package 10 may be terminally sterilized before it is placed into the box. Once the package 10 is placed into the box, the box may be stored at ambient temperature or conditions and used as needed.

In use, the package 10 of the present invention containing the specimen may be stored on shelves or refrigerated until the specimen is needed for a transplant operation or laboratory testing. The holes 78 in the inner lid 70 will help equalize the pressure between the ambient atmosphere of the cavity 20 of the outer tray and the atmosphere of the cavity 48 of the inner tray 12. Equalizing the pressure differential will help prevent the lid 70 from prematurely separating from the inner tray 12, during storage or transport.

When the specimen is needed, such as for a transplant operation, the package 10 is removed from the storage location and box. The transparent material used for both the outer tray 14 and the inner tray 12 is particularly useful in identifying the specimen that is needed. The transparent material used for the trays allows for visual inspection of the specimen without opening the package 10. This will reduce the amount of "guess work" needed in order for a person (such as a nurse or technician) to select the proper size and shape of the specimen for transplant.

The package 10 is then taken to an operating room or surgery area, where it can be opened. Under normal circumstances, the operating room will be partitioned by an imaginary line that divides the room into a sterile field and a non-sterile field. The package 10 is typically taken to the non-sterile field because the outer surface of the outer tray 14, although initially sterilized through the terminal sterilization process, may become non-sterile after it is removed from the box because the outer surface of the box. It is not uncommon for the outer surface of the box to be exposed to non-sterile conditions during shipping, storage and the like. Thus, by opening the package 10 in the non-sterile field, the risk of introducing microbial contaminants into the sterile field is reduced. Once the package 10 is in the non-sterile field, the inner tray 12 can be aseptically removed from the outer tray 14 to present the inner tray into the sterile field, such as the operating room or other sterile area.

Figure 6:
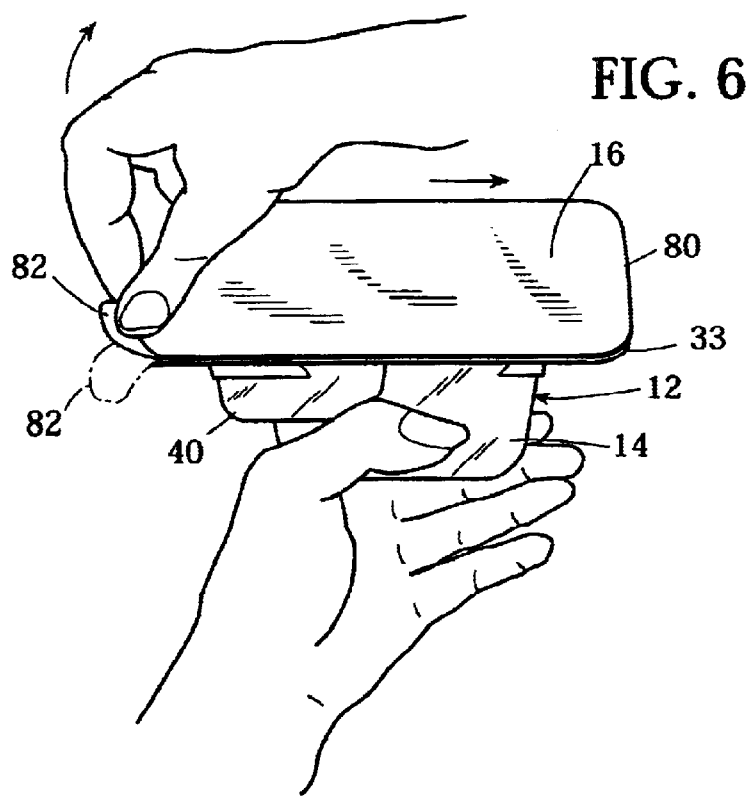

FIGS. 6 though 8 illustrate the exemplary steps taken to remove the specimen by an operating room technician. For example, as shown in FIG. 6, the blister portion of the outer tray 14 may be grasp by the left hand of the operating room technician. (It should be understood that gloves will normally be worn by the technician.) Once the outer tray 14 is grasped, the right hand can be used to peel back the outer lid 16 of the package 10. The outer lid 16 is peeled back by grasping the tab 82 between the index finger and thumb and pulling tab 82 upwardly and toward the right of the paper according to the arrows. As the tab 82 is pulled toward the right, the lid 16 will be peeled off the outer tray (illustrated in FIG. 7) to expose the inner tray 12. As the lid 16 is being peel-off to open the package 10, the tab 74 of the inner lid will automatically move from its closed, storage position (shown in FIG. 5) springing away from the lid 70 toward an upright, access position so that it can be grasped by the technician to remove the inner tray 12. To remove the inner tray 12, the technician can use his or her right hand, grasping the tab 74 between the thumb and index finger, as illustrated in FIG. 8. Once the tab 74 is grasped, the technician pulls his or her hand upwardly and to the right of the paper, as illustrated by arrows. Thereafter, the inner tray 12 can be removed from within the cavity 48 of the outer tray 14 without contacting the outer surface of the outer tray 12, which may be unsterile. In that way, the inner tray 12 remains sterile.

Once the inner tray 12 is removed, it can be introduced into the sterile field of the operating room. Once the inner tray 12 is in the sterile field, the lid 70 is peeled back to expose the specimen. Thereafter, the specimen is removed from the cavity 48 and may be deposited into a sterile basin of saline or other comparable solution for reconstitution or rehydration. As an alternative, the saline or comparable solution can be poured into the cavity of the inner tray 12 to facilitate reconstitution of the tissue. As such, the inner tray 12 can be advantageously used as a container or basin for the reconstitution of the tissue specimen. Thereafter, the surgeon may then perform some type of shaping, sizing or fine tuning of the specimen, if necessary, prior to transplant or implantation into the recipient. The package 10 may be discarded or recycled, but not reused.

The present invention may be embodied in other specific forms without departing from the spirit or essential attributes thereof and, accordingly, reference should be made to the appended claims, rather that to the foregoing specification, as indicating the scope of the invention.

We claim:

1. A package containing a sterile item, the package comprising:
    a moisture resistant outer tray having a bottom wall and a first cavity, the first cavity being defined by side walls comprising moisture barrier material and exhibiting a first pressure, the side walls supporting a first sealing element;
    an inner tray removably disposed and shaped to fit within the first cavity, the inner tray having a bottom wall and a second cavity, the second cavity being defined by side walls and exhibiting a second pressure, the side walls of the inner tray supporting a second sealing element;
    a non-porous inner lid releasably sealed to the second sealing element, the inner lid and the inner tray being arranged for enclosing the sterile item in a moisture resistant, sterile environment to prevent the sterile item from being exposed to moisture or microbial contaminants during storage;
    an outer lid releasably sealed to the first sealing element for enclosing the inner tray in a moisture resistant, sterile environment;
    wherein the sterile item comprises a human or an animal tissue specimen, the specimen having lipids.

2. The package as claimed in claim 1, wherein the sterile item is an implant comprising human or animal tissue.

3. The package as claimed in claim 2, wherein the inner lid is secured to the second sealing element by an adhesive.

4. The package as claimed in claim 3, wherein the adhesive comprises material that resists break-down when in contact with lipids associated with human or animal tissue.

5. The package as claimed in claim 1, wherein the inner lid includes a tab to facilitate removal of the inner tray from the first cavity of the outer tray.

6. The package as claimed in claim 5, wherein the tab is folded over to overlie the inner lid when the package is closed.

7. The package as claimed in claim 6, wherein the tab unfolds automatically when the package is opened.

8. The package as claimed in claim 1, wherein the outer tray has outwardly projecting lugs formed within the side walls.

9. The package as claimed in claim 8, wherein the inner tray has outwardly projecting lugs adapted to mate with the lugs of the outer tray.

10. The package as claimed in claim 1, wherein the outer tray comprises a one piece moisture barrier material.

11. The package as claimed in claim 1, wherein the inner tray comprises a one piece moisture barrier material.

12. The package as claimed in claim 1, wherein both the inner tray and the outer tray comprise moisture barrier material.

13. The package as claimed in claim 1, wherein the side walls of the inner tray are coated with a layer of moisture barrier material.

14. The package as claimed in claim 13, wherein the outer lid is made of a non-porous high moisture barrier, puncture resistant flexible laminate.

15. The package as claimed in claim 14, wherein the inner lid is made of a sheet of medical grade lidding material.

16. The package as claimed in claim 15, wherein the lidding material is non-porous high density polyethylene.

17. The package as claimed in claim 16, wherein the inner lid comprises a hole to equalize the pressure in the second cavity relative to the pressure in the first cavity so that the inner lid will not prematurely separate from the inner tray during storage or transport of the package.

18. The package as claimed in claim 17, wherein the hole is sized to equalize the pressure in the second cavity while preventing moisture from communicating from the first cavity to the second cavity to contaminate the sterile item.

19. A package containing a sterile item, the package comprising:
    an outer package having a first cavity and a first sealing element, the first cavity being defined by a plurality of first side walls comprising moisture barrier material, the first cavity exhibiting a first pressure;
    an inner package to fit within the first cavity of the outer package, the inner package having a second cavity for storing the sterile item and a second sealing element, the second cavity being defined by a plurality of second side walls comprising moisture barrier material, the second cavity exhibiting a second pressure;
    an inner lid made of sterilizable non-porous lidding material releasably sealed to the second sealing element of the inner package, the inner package and the inner lid being arranged to enclose the sterile item in a moisture and microbial resistant, sterile environment;
    an outer lid releasably secured to the first sealing element of the outer tray to enclose the inner package in a moisture resistant, sterile environment;
    wherein the sterile item comprises a tissue specimen for implantation, the tissue specimen having residual lipids.

20. The package as claimed in claim 19, wherein the second sealing element of the inner package includes a shoulder flange that projects outwardly from the second walls, the shoulder flange having an edge.

21. The package as claimed in claim 19, wherein the first sealing element of the outer package includes an outer shoulder flange that projects outwardly from the first walls, the shoulder flange having an edge.

22. The package as claimed in claim 21, wherein the outer shoulder flange is joined to the first walls by an inner shoulder flange, the inner shoulder flange being disposed in a plane located below the outer shoulder flange, thereby forming a seat having a ridge.

23. The package as claimed in claim 22, wherein the shoulder flange of the second sealing element is nested within the seat of the outer package when the package is assembled and closed.

24. The package as claimed in claim 19, further comprises a finger or thumb receiving recess portion to facilitate removal of the inner package from the outer package.

25. The package as claimed in claim 20, in which the at least one hole is sized to equalize the pressure in the second cavity while precluding cross-communication of fluids between the first cavity and the second cavity to preserve the sterility of the specimen.

26. A package containing an implantable specimen of human or animal tissue, the specimen having lipids, the package comprising:
    a moisture resistant outer tray having a first recess formed by a first wall, the first wall having moisture barrier means for resisting moisture uptake into the first recess through the wall,
    a first sealing element supported by the first wall;
    an outer lid sealingly secured to the first sealing element to provide a sealed substantially moisture resistant environment in the first recess, the sealed first recess exhibiting a first pressure value;
    a moisture resistant inner tray removable disposed within the first recess of the outer tray, the inner tray having a second recess for storing the specimen, the second recess being formed by a second wall;
    a second sealing element supported by the second wall;
    an inner lid made of terminally sterilizable non-porous material sealingly secured to the second sealing element to moisture seal the second recess of the inner tray, the sealed second recess exhibiting a second pressure value, the inner lid having at least one hole to equalize the second pressure value in the second recess of the inner tray relative to the first pressure value in the first recess of the outer tray so that the inner lid will not prematurely separate from the inner tray due to the pressure differential between the pressure values in the inner tray and the outer tray recesses;
    wherein the implantable specimen of the sterile item has lipids and the moisture resistant inner tray and the moisture resistant outer tray are arranged to enclose the sterile item in a moisture resistant sterile environment to prevent the sterile item from being exposed to moisture or microbial contaminants during storage.

27. The package as claimed in claim 26, further comprising a tab secured to the inner lid, the tab being foldable to overlie the inner lid when the inner lid is enclosed in the first recess of the outer tray by the outer lid, the tab being arranged for automatically unfolding when the inner tray is removed from the recess of the outer tray.

28. The package as claimed in claim 26, wherein the second sealing element comprises an adhesive that resists breakdown when contacted by lipids.

29. The package as claimed in claim 26, wherein the inner lid is made from medical grade lidding material.

30. A storage unit containing a sterile item comprising a human or an animal tissue specimen, the storage unit comprising:
    a first three-dimensional package having a first recess exhibiting a first pressure, the first package including means for resisting moisture uptake into the first recess;

a second three-dimensional package removably disposed within the first recess, the second package having a second recess exhibiting a second pressure;

a first lid releasably secured to the first package for moisture and pressure sealingly enclosing the second package within the first recess of the first package;

a non-porous second lid releasably secured to the second package, the second lid and the second package being arranged for moisture and pressure sealingly enclosing the sterile item in the second recess and including means to equalize the pressure of the first recess relative to the pressure of the second recess in the presence of a pressure differential between the first and second pressure so that the inner lid will not prematurely separate from the inner tray in response to the pressure differential;

wherein the sterile item comprises a human or an animal tissue specimen and the second lid and the second package are arranged for moisture and pressure sealingly enclosing the sterile item in a moisture resistant, sterile environment when the storage unit is stored.

31. The storage unit as claimed in claim 30, wherein the second package includes a moisture resistant means for preventing moisture or microbial contaminants from being absorbed from the ambient atmosphere external the second package by the sterile item stored in the recess.

32. The storage unit as claimed in claim 31, wherein the moisture resisting means of the first package comprises at least approximately about 2 mm of moisture barrier material or less.

33. The storage unit as claimed in claim 30, wherein the first package includes moisture resistant means for preventing moisture or microbial contaminants from being absorbed from the ambient atmosphere external to the first package.

34. The storage unit as claimed in claim 33, wherein the moisture resistant means of the first package comprises a film of moisture barrier material that has a moisture transition rate of approximately about 0.011 g/m2 per 24 hours.

35. The storage unit as claimed in claim 30, wherein the first package comprises a transparent sheet of semi-rigid, flexible thermoformable plastic resin having moisture barrier properties.

36. A storage unit containing an implantable specimen comprising a human or an animal allograft having lipids, the storage unit comprising:

an outer package comprising a non-porous thermoplastic sheet of material coated with a film of moisture barrier material, the coated sheet of material being formed into a three-dimensional object from a flat sheet, the object having a first recess for releasably storing an item in a moisture resistant, sterile environment;

an inner package made from a sheet of non-porous material that is formed into a three-dimensional object that is shaped to fit within the recess of the outer package, the inner package having a second recess to store the specimen;

a non-porous inner lid releasably sealed to the inner package for enclosing the specimen in a moisture resistant, sterile environment to prevent the sterile item from being exposed to microbial contaminants;

an outer lid releasably sealed to the outer package for enclosing the inner package in a moisture and microbial resistant, sterile environment;

wherein the implantable specimen comprises a human or an animal allograft having lipids, such that the inner package and the inner package are arranged for enclosing the implantable specimen in a moisture resistant, sterile environment to prevent the implantable specimen from being exposed to moisture or microbial contaminants during storage.

37. The package as claimed in claim 36, wherein the package is terminally sterilized.

38. A terminally sterilizable package for storing and transporting an allograft specimen for implantation or transplant, the specimen having lipids, the package comprising:

a moisture resistant outer tray having a bottom wall and a first cavity, the first cavity being defined by first side walls comprising moisture barrier material and exhibiting a first pressure, the first side walls supporting a first sealing element;

an inner tray removably disposed and shaped to fit within the first cavity, the inner tray having a bottom wall and a second cavity, the second cavity being defined by second side walls and exhibiting a second pressure, the side walls of the inner tray supporting a second sealing element;

a non-porous inner lid releasably sealed to the second sealing element the inner lid and inner tray being arranged for enclosing the specimen in a moisture resistant, sterile environment to prevent the sterile item from being exposed to moisture microbial contaminants during storage, the inner lid including a tab that is folded over to overlie the inner lid when the package is closed; and an outer lid made of non-porous material releasably sealed to the first sealing element for enclosing the inner tray in a moisture resistant sterile environment.

39. The package as claimed in claim 38, further comprising at least one hole to equalize the pressure in the second cavity relative to the pressure in the first cavity so that the inner lid will not prematurely separate from the inner tray.

40. The package as claimed in claim 39, wherein the outer tray includes a thumb receiving portion to facilitate removal of the inner tray from the outer tray.

41. The package as claimed in claim 40, wherein the outer tray is made from a transparent sheet of semi-rigid, flexible material.

42. The package as claimed in claim 41, wherein the semi-rigid material of the outer tray is coated with a layer of moisture barrier material.

43. The package as claimed in claim 42, wherein the moisture barrier material has a moisture vapor transition rate of about 0.12 grams/m$^2$/day or less.

44. The package as claimed in claim 39, wherein the first side walls are coated with a layer of moisture barrier material.

45. The package as claimed in claim 44, wherein the inner lid is made from medical grade lidding material.

46. The package as claimed in claim 45, wherein the outer lid is made of a non-porous high moisture barrier, puncture resistant flexible lamination.

47. The package as claimed in claim 45, wherein the outer lid is made with a flexible lamination comprising foil having a vapor transmission rate of about zero.

48. The package as claimed in claim 39, wherein the outer lid is made of material for withstanding sterilization by radiation and heat treatment.

49. The package as claimed in claim 48, wherein the inner lid is sealed to the second sealing element by an adhesive that resists breakdown when in contact with lipids from the specimen.

* * * * *